US00PP11679P

United States Patent [19]

Trees

[11] Patent Number: Plant 11,679

[45] Date of Patent: Dec. 12, 2000

[54] GERANIUM PLANT NAMED 'BALSHOLILA'

[75] Inventor: Scott C. Trees, Nipomo, Calif.

[73] Assignee: Ball Floraplant, a division of Ball Horticultural Co., West Chicago, Ill.

[21] Appl. No.: 09/255,311

[22] Filed: Feb. 22, 1999

[51] Int. Cl.[7] ..... A01H 5/00

[52] U.S. Cl. ..... Plt./329

[58] Field of Search ..... Plt./329, 325, 328

*Primary Examiner*—Howard J. Locker
*Assistant Examiner*—Wendy A Baker
*Attorney, Agent, or Firm*—C. A. Whealy

[57] ABSTRACT

A new and distinct cultivar of Geranium plant named 'Balsholila', characterized by its numerous semi-double medium purplish pink-colored flowers with a white "eye"; upright growth habit; good basal branching; good vigor; and dark green leaves.

1 Drawing Sheet

BACKGROUND OF THE INVENTION

The present invention relates to a new and distinct cultivar of Geranium plant, botanically known as *Pelargonium×hortorum*, and hereinafter referred to by the cultivar name Balsholila.

The new Geranium is a product of a planned breeding program conducted by the Inventor in Arroyo Grande, Calif. The objective of the breeding program was to develop new cultivars with freely-branching growth habit, dark green-colored foliage, uniform flowering, and interesting flower and foliage colors.

The new Geranium originated from a cross made by the Inventor of the proprietary *Pelargonium×hortorum* selection BFP-1006 as the male, or pollen parent, with the proprietary *Pelargonium×hortorum* selection BFP-760 as the female, or seed parent. The cultivar Balsholila was discovered and selected by the Inventor as a flowering plant within the progeny of the stated cross in a controlled environment in Arroyo Grande, Calif., in January, 1996.

Asexual reproduction of the new cultivar by terminal cuttings taken at Arroyo Grande, Calif., has shown that the unique features of this new Geranium are stable and reproduced true to type in successive generations of asexual reproduction.

SUMMARY OF THE INVENTION

The following traits have been repeatedly observed and are determined to be the unique characteristics of 'Balsholila'. These characteristics in combination distinguish 'Balsholila' as a new and distinct cultivar:

1. Numerous semi-double medium-purplish pink-colored flowers with a white "eye".

2. Upright growth habit.

3. Good basal branching and vigorous.

4. Dark green leaves.

The new Geranium can be compared to the cultivar, Clips Light Lavender, disclosed in U.S. Plant Pat. No. 10,349. However, in side-by-side comparisons conducted in Arroyo Grande, Calif., plants of the new Geranium differ from plants of the cultivar Clips Light Lavender in the following characteristics:

1. Plants of the new Geranium are broader than plants of the cultivar Clips Light Lavender.

2. Plants of the new Geranium are more vigorous than plants of the cultivar Clips Light Lavender.

3. Plants of the new Geranium have larger leaves than plants of the cultivar Clips Light Lavender.

4. Plants of the new Geranium have larger flowers than plants of the cultivar Clips Light Lavender.

5. Plants of the new Geranium have more flowers per umbel than plants of the cultivar Clips Light Lavender.

6. Flower color of plants of the new Geranium is slightly lighter than flower color of plants of the cultivar Clips Light Lavender.

Plants of the new Geranium have larger sepals than plants of the cultivar Clips Light Lavender.

A detailed comparison of plants of the cultivar Balsholila and the cultivar Clips Light Lavender, as grown side by side, appears in Chart A at the end of the specification.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical plant of 'Balsholila'. Flower and foliage colors in the photograph may appear different from the actual colors due to light reflectance.

DETAILED BOTANICAL DESCRIPTION

The cultivar Balsholila has not been observed under all possible environmental conditions. The phenotype may vary somewhat with variations in environment such as temperature and light intensity, without, however, any variance in genotype. The following observations, measurements and comparisons describe plants grown in 10-cm pots in Arroyo Grande, Calif., under commercial practice in a glass-covered greenhouse with day temperatures about 20° to 22° C., night temperatures about 18° to 20° C. and light levels generally about 2,500 to 3,000 footcandles.

In the following description, color references are made to The Royal Horticultural Society Colour Chart except where general terms of ordinary dictionary significance are used.

Botanical classification: *Pelargonium×hortorum* cultivar Balsholila.

Parentage:

*Male parent*.—Proprietary *Pelargonium×hortorum* selection BFP-1066.

*Female parent*.—Proprietary *Pelargonium×hortorum* selection BFP-760.

Propagation:

*Type cutting*.—Terminal cuttings.

*Time to initiate roots*.—About 7 days at 18° C.

*Time to develop roots*.—About 21 days at 18° C.

*Rooting habit*.—Fibrous and freely branching.

Plant description:

*General appearance*.—Upright growth habit. Appropriate for 10 and 12.5-cm containers.

*Crop time*.—Starting with a rooted cutting, about eight weeks are required to produced a finished flowering plant in 10-cm container.

*Growth and branching habit*.—Vigorous and good basal branching with about three lateral branches at the base. Pinching, that is, removal of the terminal apex, is usually not required.

*Plant height* (*to top of foliage*).—About 10 to 12 cm.

*Plant width*.—About 16 to 17 cm.

*Lateral branches*.—Length: About 7 to 10 cm. Internode length: About 1 to 1.5 cm. Color: 146A.

*Foliage description*.—Leaves simple, generally symmetrical, abundant, opposite. Quantity of leaves per lateral branch: About 8 to 11. Length: About 4.5 to 5.2 cm. Width: About 6.7 to 9 cm. Shape: Reniform. Apex: Rounded. Base: Cordate. Margin: Crenate. Venation: Palmate. Texture: Both surfaces slightly pubescent. Color: Young foliage, upper surface: Slightly lighter than 147A. Young foliage, lower surface: Slightly lighter than 147B. Fully expanded foliage, upper surface: 147A or darker than 147B with very faint, slightly darker, zonation pattern, about 2 cm wide. Fully expanded foliage, lower surface: 147B. Venation, upper surface 143C. Venation, lower surface: 143C. Petiole: Length: About 5 to 7 cm. Diameter: About 2 to 3 mm. Color: 146A.

Flower description:

*Flower type and habit*.—Medium purplish pink-colored flowers with a white "eye". Freely and continuously flowering. Flowers arranged in hemispherical to generally hemispherical umbels arising from apical leaf axils. Umbels displayed above or beyond the foliage. At full flowering, usually about three or four open umbels and about three developing umbels per plant. Flowers semi-double and round. Umbels persistent. Not fragrant.

*Flowering season*.—Year-round under greenhouse conditions. In the garden, flowering is continuous from spring until fall.

*Umbels*.—Number of flowers per umbel: About 25 to 35. Diameter: About 9 to 10 cm. Height: About 6 to 7 cm.

*Flowers*.—Diameter: About 4.8 to 5.3 cm. Depth (height): About 1.5 cm.

*Flower buds*.—Length: About 1.4 to 1.6 cm. Diameter: About 6.5 to 7 mm. Shape: Oval, pointed.

*Petals*.—Quantity: About 6 to 8 petals and about 2 to 3 elongated petaloids per flower. Arrangement: Imbricate. Length: About 2.5 to 3 cm. Width: About 2.3 to 2.8 cm. Shape: Obovate. Apex: Rounded. Base: Attenuate. Margin: Entire. Texture: Smooth, iridescent. Color, fully opened flowers: Upper two or three petals, upper surface: Between 68B and 68C; venation, 68A; towards base, 155D. Upper two petals, lower surface: 73D; venation, 68A. Lower petals, upper surface: Between 68B and 68C; venation, 68A. Lower petals, lower surface: 73D; venation, 68A.

*Sepals*.—Quantity: About 5, imbricate. Length: About 1.4 to 1.5 cm. Width: About 3 to 4 mm. Shape: Lanceolate. Apex: Pointed. Margin: Entire. Texture: Smooth. Color, upper and under surfaces: 146A.

*Peduncle* (*umbel stem*).—Length: About 12 to 16 cm. Angle: Erect. Strength: Strong. Texture: Pubescent. Color: Young, 146A; mature, 187A. *Pedicel* (*individual flower stem*).—Length: About 3 to 3.5 cm. Angle: Erect. Strength: Moderately strong. Texture: Pubescent. Color: 146A.

*Reproductive organs*.—Androecium: Anther size: About 1.5 to 2 mm. Pollen amount: Moderate. Pollen color: 31A. Gynoecium: Ovary color: Green.

Disease resistance: Resistance to pathogens common to Pelargonium has not been observed.

Seed development: Seed production has not been observed.

CHART A

| CHARACTERISTIC | 'BALSHOLILA' | 'CLIPS LIGHT LAVENDER' |
|---|---|---|
| PLANT HEIGHT (to top of foliage) | About 10 to 12 cm | About 10 to 12 cm |
| PLANT WIDTH | About 16 to 17 cm | About 10 to 12 cm |
| LATERAL BRANCH LENGTH | About 7 to 10 cm | About 5 to 9 cm |
| VIGOR | Vigorous | Moderately vigorous |
| LEAF LENGTH | About 4.5 to 5.2 cm | About 4.1 to 4.3 cm |
| LEAF WIDTH | About 6.7 to 9 cm | About 6.3 to 7.3 cm |
| PETIOLE LENGTH | About 5 to 7 cm | About 4 to 5.8 cm |
| PETIOLE DIAMETER | About 2 to 3 mm | About 1.5 to 2 mm |
| UMBEL DIAMETER | About 9 to 10 cm | About 7.8 to 9 cm |
| NUMBER OF FLOWERS PER UMBEL | About 25 to 35 | About 15 to 25 |
| FLOWER DIAMETER | About 4.8 to 5.3 cm | About 4.3 to 4.8 cm |
| FLOWER DEPTH | About 1.5 cm | About 2 cm |
| PETAL COLOR, UPPER PETALS, UPPER SURFACE | Between 68B and 68C; venation, 68A; towards base, 155D | Between 68A and 68B; venation, 68A; towards base, 155D |
| PETAL COLOR, UPPER PETALS, LOWER SURFACE | 73D; venation, 68A | 73D; venation, 68A |
| PETAL COLOR, LOWER PETALS, UPPER SURFACE | Between 68B and 68C; venation, 68A | Between 68A and 68B; venation, 68A |
| PETAL COLOR, LOWER PETALS, LOWER SURFACE | 73D; venation, 68A; | 73D; venation, 68A |
| SEPAL LENGTH | About 1.4 to 1.5 cm | About 1.1 to 1.2 cm |
| SEPAL WIDTH | About 3 to 4 mm | About 2 to 3 mm |

It is claimed:

1. A new and distinct cultivar of Geranium plant named 'Balsholila', as illustrated and described.

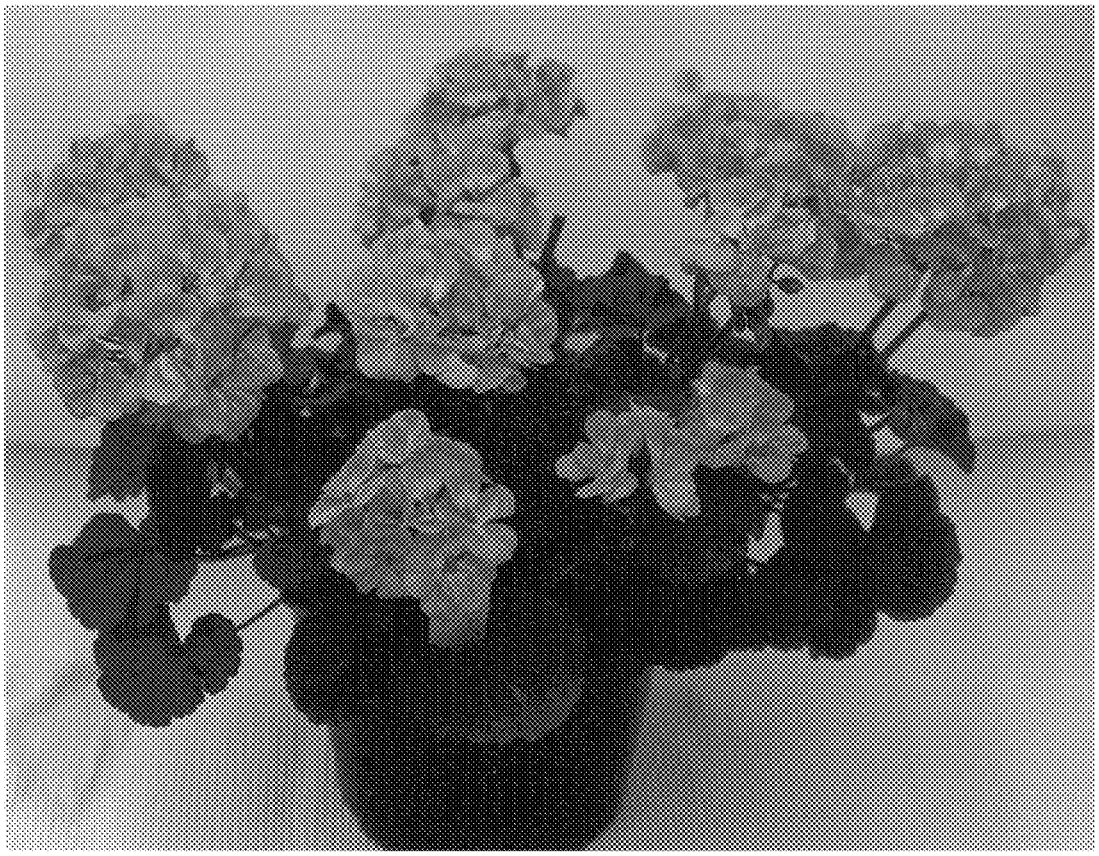

* * * * *